United States Patent
Memo et al.

(10) Patent No.: US 11,208,473 B2
(45) Date of Patent: *Dec. 28, 2021

(54) ANTIBODY BINDING A LINEAR EPITOPE OF HUMAN P53 AND DIAGNOSTIC APPLICATIONS THEREOF

(71) Applicant: Diadem S.r.l., Brescia (IT)

(72) Inventors: Maurizio Memo, Monticelli Brusati (IT); Daniela Uberti, Brescia (IT)

(73) Assignee: Diadem S.r.l., Brescia (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/093,541

(22) Filed: Nov. 9, 2020

(65) Prior Publication Data

US 2021/0070848 A1 Mar. 11, 2021

Related U.S. Application Data

(63) Continuation of application No. 16/214,455, filed on Dec. 10, 2018, now Pat. No. 10,875,908, which is a continuation of application No. 15/515,693, filed as application No. PCT/EP2015/072094 on Sep. 25, 2015, now Pat. No. 10,183,990.

(30) Foreign Application Priority Data

Sep. 30, 2014 (IT) .............................. TO2014000776

(51) Int. Cl.
*C07K 16/18* (2006.01)
*C07K 16/32* (2006.01)
*G01N 33/68* (2006.01)

(52) U.S. Cl.
CPC .............. *C07K 16/18* (2013.01); *C07K 16/32* (2013.01); *G01N 33/6896* (2013.01); *C07K 2317/34* (2013.01); *G01N 2333/4748* (2013.01); *G01N 2800/2821* (2013.01); *G01N 2800/56* (2013.01); *G01N 2800/7042* (2013.01)

(58) Field of Classification Search
None
See application file for complete search history.

(56) References Cited

U.S. PATENT DOCUMENTS

| | | | |
|---|---|---|---|
| 7,833,513 | B2 | 11/2010 | de la Monte et al. |
| 8,703,734 | B2 | 4/2014 | Lyakhov et al. |
| 10,183,990 | B2 | 1/2019 | Memo et al. |
| 10,875,908 | B2 | 12/2020 | Memo et al. |
| 2006/0188951 | A1 | 8/2006 | Mook et al. |
| 2009/0311278 | A1 | 12/2009 | Evans et al. |
| 2012/0082667 | A1 | 4/2012 | Yokoseki et al. |
| 2015/0147343 | A1 | 5/2015 | Nitsch et al. |
| 2018/0057572 | A1 | 3/2018 | Memo et al. |
| 2019/0194305 | A1 | 6/2019 | Memo et al. |

FOREIGN PATENT DOCUMENTS

| | | |
|---|---|---|
| RU | 2174409 C2 | 10/2001 |
| WO | 94/12202 A1 | 6/1994 |
| WO | 00/32175 A2 | 6/2000 |
| WO | 2007/123723 A2 | 11/2007 |
| WO | 2008/147186 A1 | 12/2008 |
| WO | 2010037395 A2 | 4/2010 |

OTHER PUBLICATIONS

Abate "A Conformation Variant of p53 Combined with Machine Learning Identifies Alzheimer Disease in Preclinical and Prodromal Stages" J. Pers. Med. 2021, 11, 14 (Year: 2021).*
Buizza et al., "Conformational Altered p53 as an Early Marker of Oxidative Stress in Alzheimer's Disease", PLOS ONE, vol. 7, Issue 1, Jan. 5, 2012, p. e29789 (11 pages).
Buizza et al., "Conformational altered p53 affects neuronal function: relevance for the response to toxic insult and growth-associated protein 43 expression", Cell Death and Disease, vol. 4, No. 2, Feb. 1, 2013, p. e484 (10 pages).
Canevelli et al., "Cognitive frailty: what is still missing?" The Journal of Nutrition, Health and Aging 19(3):273-5 (abstract only) (Year: 2015).
Carter, J.M., "Conjugation of peptides to carrier proteins via glutaraldehyde", book chapter from The Protein Protocols Handbook p. 679-687, Jan. 1996.
Chen et al., "Enhancement and destruction of antibody function by somatic mutation: unequal occurrence is controlled by V gene combinatorial associations" EMBO Journal vol. 14 No. 1 2 pp. 2784-2794 (Year: 1995).
Danks et al., "Differences in epitope accessibility of p53 monoclonal antibodies suggest at least three conformations ar states of protein binding of p53 protein in human tumor cell lines", Cell Death and Differentiation, vol. 5, No. 8, Aug. 1, 1998, pp. 678-686.
Fujiwara et al., "A compound CP-31398 suppresses excitotoxicity-induced neurodegeneration", Biochemical and Biophysical Research Communications, vol. 440, No. 3, Aug. 26, 2013, pp. 359-363.
Google "epitope" accessed from google.com on Dec. 31, 2018 (Year: 2018).
Hupp, "Regulation of p53 protein function through alterations in protein-folding pathways", CMLS Cellular and Molecular Life Sciences, vol. 55, No. 1, Jan. 1, 1999, pp. 88-95.
International Search Report for International Application No. PCT/EP2015/072094, dated Dec. 16, 2015 (4 pages).

(Continued)

*Primary Examiner* — Adam Weidner
(74) *Attorney, Agent, or Firm* — Nutter McLennen & Fish LLP

(57) ABSTRACT

The invention relates to an anti-human p53 antibody suitable for specifically binding a linear epitope which is exposed only in a conformationally altered isoform of the characteristic p53 protein of patients with Alzheimer's disease or prone to develop Alzheimer's disease or cognitive impairment during ageing. Methods and diagnostic and prognostic kits are also described.

10 Claims, 5 Drawing Sheets
Specification includes a Sequence Listing.

(56) References Cited

OTHER PUBLICATIONS

Kelaiditi et al., "Cognitive frailty: Rational and definition from an (I.AN.A/I.A.G.G.) International Consensus Group" The Journal of Nutrition, Health, and Aging 17(9):726-34 (abstract only) (Year: 2013).

Kussie et al., "A Single Engineered Amino Acid Substitution Changes Antibody Fine Specificity" J immunol 152(1): 146-52 (Year: 1994).

Lee B-S et al., "Production of antipeptide antibodies", Methods in molecular biology (Clifton, N.J.), Jun. 2010.

Memo et al., "A conformational specific anti p53 monoclonal antibody able to recognize population at risk to develop Alzheimer's disease", BioVaria, Munich 2015, Jun. 1, 2015 (3 pages).

Russian Search Report, dated Apr. 25, 2019 (2 pages).

Uberti et al., "Identification of a mutant-like conformation of p53 in fibroblasts from sporadic Alzheimer's disease patients". Neurobiology of Aging, vol. 27, No. 9, Sep. 1, 2006, pp. 1193-1201.

Vojtesek et al., "Conformational changes in p53 analyzed using new antibodies to the core DNA binding domain of the protein", Oncogene, Nature Publish Group, vol. 10, No. 2, Jan. 19, 1995, pp. 389-393.

Walters et al., "Clinical, Molecular and Genetic Validation of a Murine Orthotopic Xenograft Model of Pancreatic Adenocarcinoma Using Fresh Human Specimens", Plos One, vol. 8, Issue 10, Oct. 2013, pp. 1-10.

International Preliminary Report on Patentability for International Application No. PCT/EP2015/072094, dated Apr. 4, 2017 (6 pages).

* cited by examiner

FIG.1

MEEPQSDPSV EPPLSQETFS DLWKLLPENN VLSPLPSQAM
DDLMLSPDDI EQWFTEDPGP DEAPRMPEAA PPVAPAPAAP TPAAPA-
PAPS WPLSSSVPSQ KTYQGSYGFR LGFLHSGTAK SVTCTYSPAL
NKMFCQLAKT CPVQLWVDST PPPGTRVRAA MYKQSQHMTE
VVRRCPHHER CSDSDGLAPP QHLIRVEGNL RVEYLDDRNT
FRHSVVVPYE PPEVGSDCTT IHYNYMCNSS CMGGMNRRPI LTIIT-
LEDSS GNLLGRNSFE VRVCACPGRD RRTEEENLRK KGEPHHELPP
GSTKRA PNN TSSSPQPKKK PLDGEYFTLQ IRGRERFEMF RELNEA-
LELK DAQAGKEPGG SRAHSSHLKS KKGQSTSRHK KLMFKTEGPD SD

SEQ ID NO: 3 cont vs SAD * p<0,01
cont vs FAD # p<0,05

FIG.3
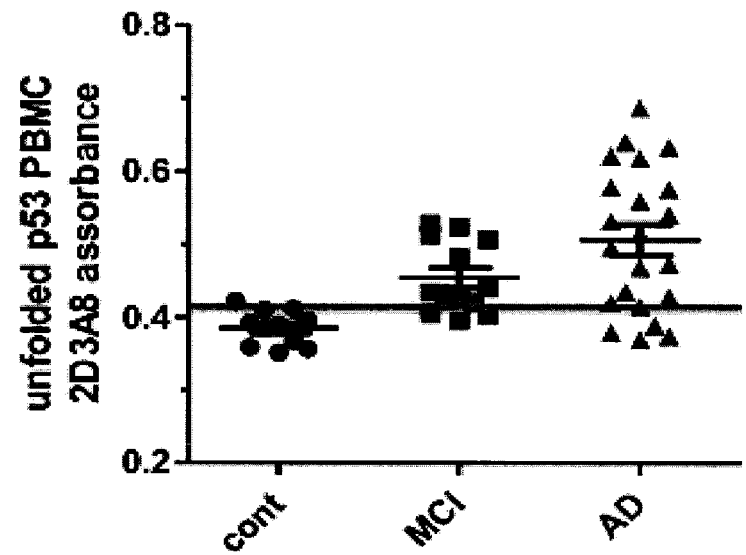
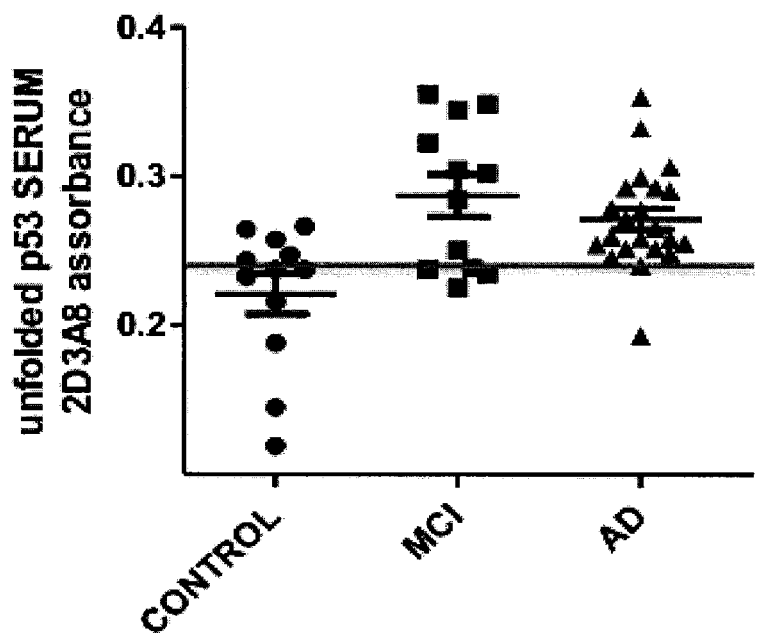

SEQUENCE LISTING

```
<160> NUMBER OF SEQ ID NOS: 13

<210> SEQ ID NO 1
<211> LENGTH: 16
<212> TYPE: PRT
<213> ORGANISM: Homo sapiens

<400> SEQUENCE: 1

Arg Arg Thr Glu Glu Glu Asn Leu Arg Lys Lys Gly Glu Pro His His
1               5                   10                  15

<210> SEQ ID NO 2
<211> LENGTH: 16
<212> TYPE: PRT
<213> ORGANISM: Homo sapiens

<400> SEQUENCE: 2

Cys Arg Thr Glu Glu Glu Asn Leu Arg Lys Lys Gly Glu Pro His His
1               5                   10                  15

<210> SEQ ID NO 3
<211> LENGTH: 392
<212> TYPE: PRT
<213> ORGANISM: Homo sapiens

<400> SEQUENCE: 3

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
                20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
        50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95
```

Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
        130                 135                 140

Leu Trp Val Asp Ser Thr Pro Pro Gly Thr Arg Val Arg Ala Ala
145                 150                 155                 160

Ile Tyr Lys Gln Ser Gln His Met Thr Glu Val Val Arg Arg Cys Pro
                165                 170                 175

His His Glu Arg Cys Ser Asp Ser Asp Gly Leu Ala Pro Pro Gln His
            180                 185                 190

Leu Ile Arg Val Glu Gly Asn Leu Arg Val Glu Tyr Leu Asp Asp Arg
        195                 200                 205

Asn Thr Phe Arg His Ser Val Val Pro Tyr Glu Pro Pro Glu Val
210                 215                 220

Gly Ser Asp Cys Thr Thr Ile His Tyr Asn Tyr Met Cys Asn Ser Ser
225                 230                 235                 240

Cys Met Gly Gly Met Asn Arg Arg Pro Ile Leu Thr Ile Ile Thr Leu
                245                 250                 255

Glu Asp Ser Ser Gly Asn Leu Leu Gly Arg Asn Ser Phe Glu Val Arg
            260                 265                 270

Val Cys Ala Cys Pro Gly Arg Asp Arg Arg Thr Glu Glu Asn Leu
        275                 280                 285

Arg Lys Lys Gly Glu Pro His His Glu Leu Pro Pro Gly Ser Thr Lys
290                 295                 300

Arg Ala Leu Pro Asn Asn Thr Ser Ser Ser Pro Gln Pro Lys Lys Lys
305                 310                 315                 320

Pro Leu Asp Gly Glu Tyr Phe Thr Leu Gln Ile Arg Gly Arg Glu Arg
                325                 330                 335

Phe Glu Met Phe Arg Glu Leu Asn Glu Ala Leu Glu Leu Lys Asp Ala
            340                 345                 350

Gln Ala Gly Lys Glu Pro Gly Gly Ser Arg Ala His Ser Ser His Leu
        355                 360                 365

Lys Ser Lys Lys Gly Gln Ser Thr Ser Arg His Lys Lys Leu Met Phe
370                 375                 380

Lys Thr Glu Gly Pro Asp Ser Asp
385                 390

<210> SEQ ID NO 4
<211> LENGTH: 572
<212> TYPE: PRT
<213> ORGANISM: Mouse

<400> SEQUENCE: 4

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
        50                  55                  60

Lys Gly Lys Ala Thr Leu Thr Ser Asp Lys Ser Ser Ser Thr Ala Tyr
65                  70                  75                  80

```
Met Glu Leu Ser Ser Leu Thr Ser Glu Asp Ser Ala Val Tyr Tyr Cys
                 85                  90                  95

Ala Arg Gly Gly Tyr Tyr Ala Met Asp Tyr Trp Gly Gln Gly Thr Ser
            100                 105                 110

Val Thr Val Ser Ser Glu Ser Gln Ser Phe Pro Asn Val Phe Pro Leu
        115                 120                 125

Val Ser Cys Glu Ser Pro Leu Ser Asp Lys Asn Leu Val Ala Met Gly
    130                 135                 140

Cys Leu Ala Arg Asp Phe Leu Pro Ser Thr Ile Ser Phe Thr Trp Asn
145                 150                 155                 160

Tyr Gln Asn Asn Thr Glu Val Ile Gln Gly Ile Arg Thr Phe Pro Thr
                165                 170                 175

Leu Arg Thr Gly Gly Lys Tyr Leu Ala Thr Ser Gln Val Leu Leu Ser
            180                 185                 190

Pro Lys Ser Ile Leu Glu Gly Ser Asp Glu Tyr Leu Val Cys Lys Ile
        195                 200                 205

His Tyr Gly Gly Lys Asn Arg Asp Leu His Val Pro Ile Pro Ala Val
    210                 215                 220

Ala Glu Met Asn Pro Asn Val Asn Val Phe Val Pro Pro Arg Asp Gly
225                 230                 235                 240

Phe Ser Gly Pro Ala Pro Arg Lys Ser Lys Leu Ile Cys Glu Ala Thr
                245                 250                 255

Asn Phe Thr Pro Lys Pro Ile Thr Val Ser Trp Leu Lys Asp Gly Lys
            260                 265                 270

Leu Val Glu Ser Gly Phe Thr Thr Asp Pro Val Thr Ile Glu Asn Lys
        275                 280                 285

Gly Ser Thr Pro Gln Thr Tyr Lys Val Ile Ser Thr Leu Thr Ile Ser
    290                 295                 300

Glu Ile Asp Trp Leu Asn Leu Asn Val Tyr Thr Cys Arg Val Asp His
305                 310                 315                 320

Arg Gly Leu Thr Phe Leu Lys Asn Val Ser Ser Thr Cys Ala Ala Ser
                325                 330                 335

Pro Ser Thr Asp Ile Leu Thr Phe Thr Ile Pro Pro Ser Phe Ala Asp
            340                 345                 350

Ile Phe Leu Ser Lys Ser Ala Asn Leu Thr Cys Leu Val Ser Asn Leu
        355                 360                 365

Ala Thr Tyr Glu Thr Leu Asn Ile Ser Trp Ala Ser Gln Ser Gly Glu
    370                 375                 380

Pro Leu Glu Thr Lys Ile Lys Ile Met Glu Ser His Pro Asn Gly Thr
385                 390                 395                 400

Phe Ser Ala Lys Gly Val Ala Ser Val Cys Val Glu Asp Trp Asn Asn
                405                 410                 415

Arg Lys Glu Phe Val Cys Thr Val Thr His Arg Asp Leu Pro Ser Pro
            420                 425                 430

Gln Lys Lys Phe Ile Ser Lys Pro Asn Glu Val His Lys His Pro Pro
        435                 440                 445

Ala Val Tyr Leu Leu Pro Pro Ala Arg Glu Gln Leu Asn Leu Arg Glu
    450                 455                 460

Ser Ala Thr Val Thr Cys Leu Val Lys Gly Phe Ser Pro Ala Asp Ile
465                 470                 475                 480

Ser Val Gln Trp Leu Gln Arg Gly Gln Leu Leu Pro Gln Glu Lys Tyr
                485                 490                 495
```

-continued

```
Val Thr Ser Ala Pro Met Pro Glu Pro Gly Ala Gly Phe Tyr Phe
            500             505             510

Thr His Ser Ile Leu Thr Val Thr Glu Glu Trp Asn Ser Gly Glu
            515             520             525

Thr Tyr Thr Cys Val Val Gly His Glu Ala Leu Pro His Leu Val Thr
            530             535             540

Glu Arg Thr Val Asp Lys Ser Thr Gly Lys Pro Thr Leu Tyr Asn Val
545             550             555             560

Ser Leu Ile Met Ser Asp Thr Gly Gly Thr Cys Tyr
            565             570
```

<210> SEQ ID NO 5
<211> LENGTH: 214
<212> TYPE: PRT
<213> ORGANISM: Mouse

<400> SEQUENCE: 5

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
        210
```

<210> SEQ ID NO 6
<211> LENGTH: 117
<212> TYPE: PRT
<213> ORGANISM: mouse

<400> SEQUENCE: 6

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
                20                  25                  30
```

Val Met His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
        50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Gly Tyr Tyr Ala Met Asp Tyr Trp Gly Gln Gly Thr Ser
            100                 105                 110

Val Thr Val Ser Ser
        115

<210> SEQ ID NO 7
<211> LENGTH: 107
<212> TYPE: PRT
<213> ORGANISM: mouse

<400> SEQUENCE: 7

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105

<210> SEQ ID NO 8
<211> LENGTH: 5
<212> TYPE: PRT
<213> ORGANISM: mouse

<400> SEQUENCE: 8

Ser Tyr Val Met His
1               5

<210> SEQ ID NO 9
<211> LENGTH: 17
<212> TYPE: PRT
<213> ORGANISM: mouse

<400> SEQUENCE: 9

Tyr Ile Asn Pro Tyr Asn Asp Gly Thr Lys Tyr Asn Glu Lys Phe Lys
1               5                   10                  15

Gly

<210> SEQ ID NO 10
<211> LENGTH: 8
<212> TYPE: PRT
<213> ORGANISM: mouse

<400> SEQUENCE: 10

-continued

```
Gly Gly Tyr Tyr Ala Met Asp Tyr
1               5

<210> SEQ ID NO 11
<211> LENGTH: 11
<212> TYPE: PRT
<213> ORGANISM: mouse

<400> SEQUENCE: 11

Arg Ala Ser Gln Asp Ile Ser Asn Tyr Leu Asn
1               5                   10

<210> SEQ ID NO 12
<211> LENGTH: 7
<212> TYPE: PRT
<213> ORGANISM: mouse

<400> SEQUENCE: 12

Tyr Thr Ser Arg Leu His Ser
1               5

<210> SEQ ID NO 13
<211> LENGTH: 9
<212> TYPE: PRT
<213> ORGANISM: mouse

<400> SEQUENCE: 13

Gln Gln Gly Asn Thr Leu Pro Tyr Thr
1               5
```

ANTIBODY BINDING A LINEAR EPITOPE OF HUMAN P53 AND DIAGNOSTIC APPLICATIONS THEREOF

CROSS REFERENCE TO RELATED APPLICATION

The present application is a continuation of and claims priority to U.S. patent application Ser. No. 16/214,455, filed Dec. 10, 2018, and entitled "Antibody Binding a Linear Epitope of Human p53 and Diagnostic Applications Thereof," which is a continuation of and claims priority to U.S. patent application Ser. No. 15/515,693, filed Mar. 30, 2017, and entitled "Antibody Binding a Linear Epitope of Human p53 and Diagnostic Applications Thereof," and which issued as U.S. Pat. No. 10,183,990 on Jan. 22, 2019, which is a U.S. national stage of and claims priority to International Patent Application No. PCT/EP2015/072094, filed Sep. 25, 2015, which claims priority to and the benefit of Italian Patent Application No. TO2014A000776, filed Sep. 30, 2014.

SEQUENCE LISTING

This application contains a Sequence Listing which has been submitted electronically in ASCII format and is hereby incorporated by reference in its entirety. Said ASCII copy, created on Nov. 9, 2020, is named 121689-10103-10104-10105-seq_listing.txt and is 14 kilobytes in size.

BACKGROUND OF THE INVENTION

The present invention lies in the field of immunodiagnostics.

More particularly, the present invention relates to an antibody, a kit and in vitro methods of diagnosing Alzheimer's disease and/or the predisposition of a subject to develop Alzheimer's disease or cognitive impairment during ageing.

The DNA binding domain (DBD) of human p53 protein (aa 101-306) is characterized by high-grade conformational flexibility and contains one $Zn^{2+}$ ion coordinated by three cysteines (residues 176, 238 and 242) and one histidine (residue 179). In the wild-type isoform of human p53 protein, the aa 282-297 linear epitope is masked and therefore not available for recognition by an epitope-specific antibody.

However, because of the high-grade flexibility of its DBD domain, p53 protein can assume several conformations, which also characterize its biological activity.

In its wild-type conformation, p53 can bind DNA consensus sequences and transcribe/repress the expression of target genes. In this conformation, the protein exposes an epitope which is recognized by the commercially available, conformationally specific antibody named PAb1620.

There are several grades of conformational alteration states of p53, which correspond to different conformationally altered isoforms. Some mutations in the p53 gene cause a conformational change of the protein, which corresponds to a conformationally altered isoform capable of being recognized by commercially available, conformationally specific antibodies.

Additional conformationally altered isoforms may also derive from post-translational modifications, such as oxidation and/or nitration reactions, which alter the wild-type tertiary structure of the protein.

Buizza L. et al. ("Conformational altered p53 as an early marker of oxidative stress in Alzheimer's disease", PlosOne 7(1):e29789) and Uberti D et al. ("Identification of a mutant-like conformation of p53 in fibroblasts from sporadic Alzheimer's disease patients", Neurobiology of Aging 27 (2006) 1193-1201) both identify the expression of mutated p53 protein in patients with Alzheimer's disease, such identification having been made using the anti-p53 antibody PAb240 which binds a cryptic epitope on the amino acid residues 213-217 of p53 protein, not detectable in the wild-type p53 protein.

BRIEF SUMMARY OF THE INVENTION

The present inventors have unexpectedly found an anti-human p53 which has proved capable of specifically and selectively recognize a conformationally altered isoform of the protein resulting from its post-translational modifications, in which the aa 282-297 linear epitope is exposed.

The inventors have also unexpectedly observed that the isoform of p53 protein recognized by the antibody of the invention is peculiarly expressed in subjects with Alzheimer's disease. In particular, the conformationally altered isoform recognized by the antibody of the invention is expressed in higher amounts in biological samples—particularly in samples of blood cells, neuronal cells or other cell types, as well as in samples of biological fluids such as, for example, blood, plasma, serum, saliva, urine—of patients with Alzheimer's disease.

The inventors further observed that such conformationally altered isoform recognized by the antibody of the invention is also expressed in biological samples of subjects with Mild Cognitive Impairment (MCI).

Therefore, the antibody of the invention is a useful diagnostic and prognostic tool, for diagnosing Alzheimer's disease and for determining the predisposition of a subject with Mild Cognitive Impairment (MCI) to develop Alzheimer's disease.

Finally, the inventors observed that the expression of the p53 protein isoform positive to the antibody of the invention in a statistically significant manner correlates with the age and cognitive impairment of the subjects studied.

Therefore, the antibody of the invention is also useful for determining the predisposition of a subject to develop cognitive impairment during ageing.

BRIEF DESCRIPTION OF THE DRAWINGS

FIG. 1 discloses a P53 protein sequence;

FIG. 3 discloses experimental data of example 4 of unfolded P53 PBMC 2d3A8 absorbance versus CONT, MCI and AD;

DETAILED DESCRIPTION OF THE INVENTION

Figure 2:
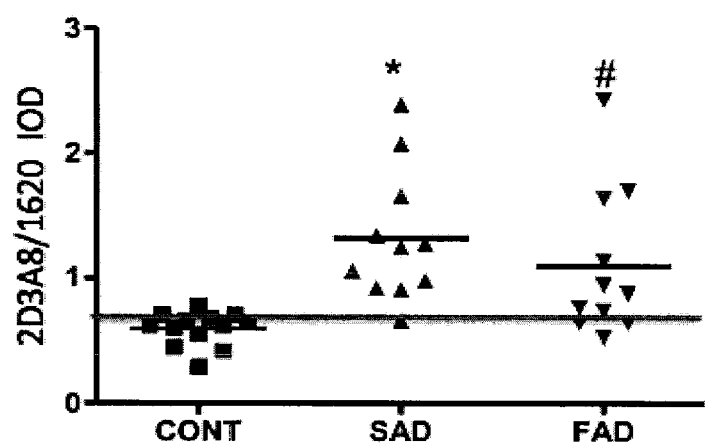
FIG. 2 discloses experimental data of 2d3A8/1620 ratio versus CONT, SAD and FAD.

A first object of the present invention is therefore an anti-human p53 antibody, characterized in that it recognizes the linear epitope of sequence RRTEEENLRKKGEPHH (SEQ ID NO:1) present in the DNA binding domain (DBD)

of human p53, said linear epitope spanning between the amino acid positions 282-297 of the amino acid sequence of human p53.

The preparation of the antibody of the invention is described in the following experimental part.

In a preferred embodiment, the antibody of the invention is a monoclonal antibody.

The antibody of the present invention can be obtained by any well-known methodology for the preparation of polyclonal or monoclonal antibodies. In the following experimental part, the preparation of the antibody by animal (mice) immunization with an antigen consisting of a peptide of sequence CRTEEENLRKKGEPHH (SEQ ID NO:2) conjugated with bovine serum albumin as carrier and hybridoma technique is described by way of example.

As previously mentioned, the antibody object of the present invention specifically recognizes an isoform of human p53 protein which has been shown to be correlated to Alzheimer's disease and development of cognitive impairment during ageing. Such antibody therefore represents a useful diagnostic and prognostic tool.

An in vitro method of determining an isoform conformationally altered by post-translational modification of p53 protein peculiar of Alzheimer's disease, as well as the diagnostic and prognostic methods as defined in the appended claims which form an integral part of the present description, are also part of the present invention.

The method detects the formation of an immunocomplex between the human p53 protein and the antibody of the sample.

An immunodiagnostic kit as defined in the appended claims is also part of the present invention.

In order to implement the methods and kit of the invention any type of well-known immunoassay can be used, such as for example immunoprecipitation assay, ELISA or RIA, immunofluorescence, Western Blot, FACS analysis, immunocytochemistry/immunohistochemistry.

An immunoassay kit may include the antibody and means for detecting the binding of the antibody to human p53 protein.

The following non-limitative examples are provided to illustrate the scope of the invention as defined by the appended claims.

Example 1

1a. Immunization

For the immunization, 6/8 week old mice which were healthy and disorder-free were used. The peptide used as antigen for antibody production had the following features:
Sequence: "N-terminal" CRTEEENLRKKGEPHH "C terminal" (SEQ ID NO: 2)
Length: 16 amino acids
Molecular weight: 1960.94
Purity: 96.4%
Form: lyophilized powder
Conjugation: Conjugated with BSA by the glutaraldehyde method The p53 protein sequence (SEQ ID NO: 3) is depicted in FIG. 1, where the DNA binding domain is highlighted in grey, and the linear epitope recognized by 2D3A8 antibody is underlined. The amino acid sequences of the 2D3A8 antibody include the heavy chain (SEQ ID NO: 4) and light chain (SEQ ID NO: 5), heavy chain variable region (SEQ ID NO: 6) and light chain variable region (SEQ ID NO: 7), heavy chain CDRs 1, 2 and 3 (SEQ ID NOS: 8, 9 and 10, respectively) and light chain CDRs 1, 2 and 3 (SEQ ID NOS: 11, 12 and 13, respectively).

The first injection has been performed by emulsifying the antigen (50 µg) in Freund's complete adjuvant (FCA). The subcutaneous injections have been performed in 2-3 sites on the animal. Additional injections have been performed at 3-week intervals with 50 µg of antigen emulsified in Freund's incomplete adjuvant (FIA). The antibody titer is evaluated by ELISA.

In the ELISA assay, the antibody titer present in the serum of 5 mice was evaluated after the third injection with the above-described peptide. The blood of immunized mice was collected from their caudal veins. The absorbance values obtained following the spectrophotometric reading provided important information on the antibody titer present in the various mice. Animals were subjected to further additional injections so that the antibody titer reached a sufficiently high level. The mouse with the best antibody titer was chosen for the first fusion.

1b. Development of Hybridomas

The animals' splenocytes were fused with mouse myeloma cells (SP2/O cell line). The fusion products were subjected to screening against the antigen to select the antibody-producing clones. The growth of these clones was continued. This first screening was performed by ELISA methodology. The positive clones were labeled as "parental clones" and frozen after 3 passages. An antigen coating was created onto ELISA plates, and successively the fusion product supernatant was added. The serum of the immunized animals was used as a positive control in ELISA (Example 2).

Example 2

After the fusion between the splenocytes of the mouse with the best antibody titer and mouse myeloma cells, an ELISA assay was performed to evaluate the fusion products. A coating with the antigen was created in a 96-well ELISA plate and serial dilutions of the supernatant from various clones were added to each well to evaluate their antibody production by spectrophotometric reading. The clones with the highest optical density at 450 nm ($OD_{450\ nm}$) were transferred to 24-well plates and after their growth the ELISA assay was repeated, the clones with the highest antibody production were transferred to 6-well plates, grown and tested again by ELISA. The procedure was repeated also for the clones transferred to culture flasks. These successive assays allowed the identification of the best clones which were tested for the last time by ELISA, with the limit dilution method to ensure that the positive clones showed an actual antibody response.

The validated antibody was purified from the supernatant of the clone with the highest $OD_{450\ nm}$ value and therefore with the best antibody titer. This antibody is named "clone 2D3A8" for brevity.

Example 3

Study of the expression of the conformationally altered isoform of p53 protein recognized by 2D3A8 antibody in patients with sporadic and familial Alzheimer's disease and MCI.

In immortalized B lymphocytes of patients diagnosed with sporadic Alzheimer (SAD) and familial Alzheimer (FAD), the conformational state of p53 was evaluated by the immunoprecipitation method, using two conformationally specific antibodies which recognize the wild-type isoform of the protein (PAb 1620) and a conformationally altered isoform (2D3A8). The immunoprecipitate was then visualized by Western Blot with a polyclonal anti-p53 antibody (CM1). The experimental data were expressed as ratio between the intensity of the band positive to 2D3A8 antibody and to PAb1620 of the same sample.

In SAD and FAD samples, the 2D3A8/1620 ratio was significantly higher compared to the lymphocytes of dementia-free control patients (FIG. 2).

2D3A8 antibody can therefore discriminate a conformationally altered isoform of p53 peculiarly expressed in immortalized lymphocytes of patients with sporadic (SAD) and familial (FAD) Alzheimer.

Example 4

In samples of fresh blood of patients diagnosed Alzheimer and of subjects with mild cognitive impairment, diagnosed MCI, the conformationally altered isoform of p53 recognized by 2D3A8 antibody (2D3A8-positive p53) was evaluated by ELISA. Healthy, dementia-free subjects of the same age were also evaluated.

2D3A8-positive p53 vas detected both in blood cells (PBMC) and in serum of the same patients or subjects. 2D3A8 antibody can recognize with high-specificity grade patients with Alzheimer. Interestingly, subjects with mild cognitive impairment express serum levels of 2D3A8-positive p53 statistically higher than the levels of protein isoform present in control subjects. In PBMCs and in serum of patients with Alzheimer, the 2D3A8-positive p53 isoform was statistically increased compared to the controls (FIG. 3).

Example 5

The 2D3A8-positive p53 isoform correlates with age.

Figure 4:
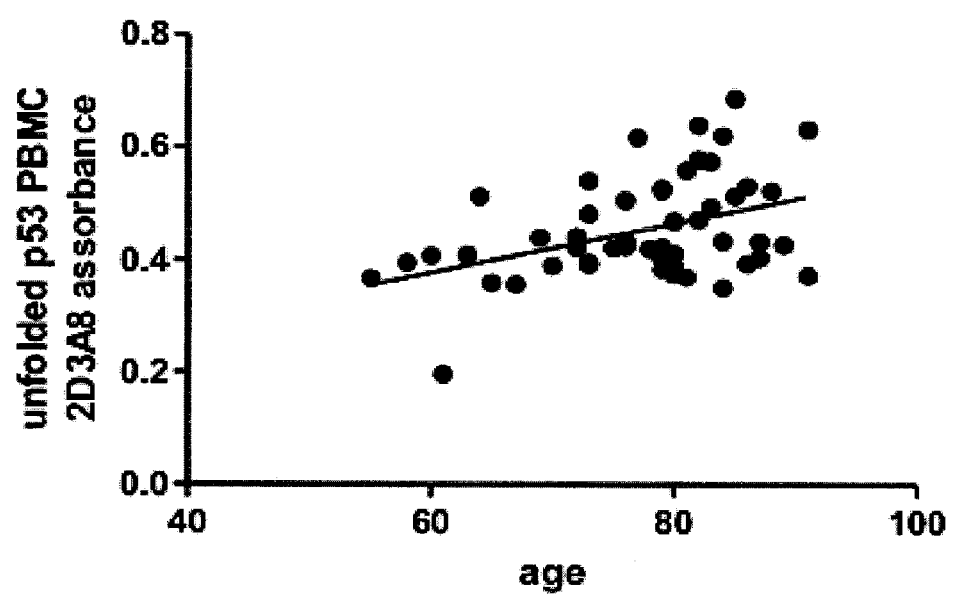
FIG. 4 discloses experimental data of example 5, during ageing, of unfolded P53 PBMC 2d3A8 absorbance versus CONT, MCI and AD.

During ageing, the expression of 2D3A8-positive p53 in blood cells (PBMC) increases in a statistically significant manner (FIG. 4).

Figure 5:
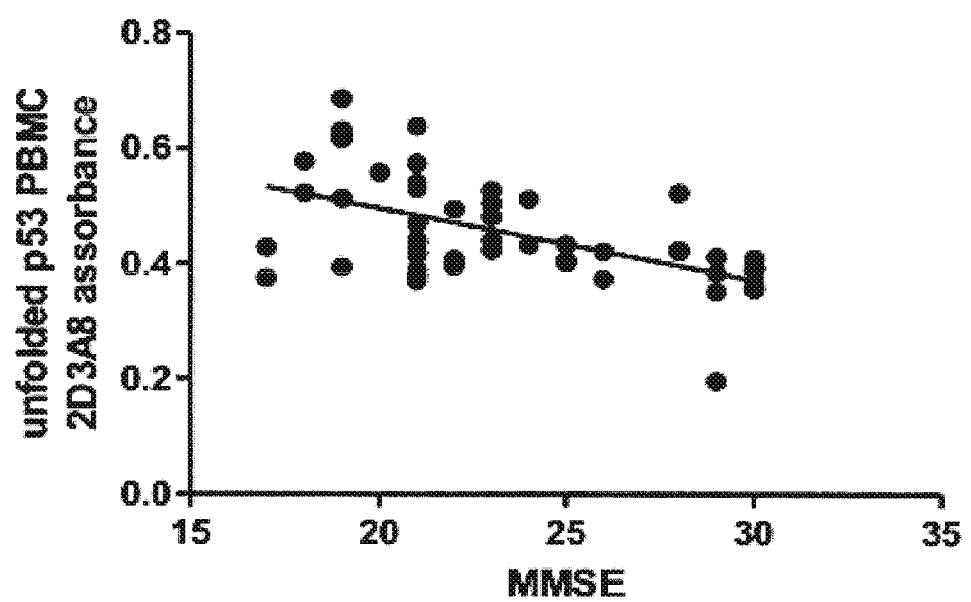
FIG. 5 discloses experimental data of example 5, decreasing of the scoring in the MMSE test, of unfolded P53 PBMC 2d3A8 absorbance versus CONT, MCI and AD.

Moreover, the expression of 2D3A8-positive p53 correlates with the cognitive status, measured by the well-known neuropsychological test MMSE. The 2D3A8-positive p53 isoform increases with the decrease of the scoring obtained in the MMSE test, i.e., it increases with the progression of cognitive impairment (FIG. 5).

The invention claimed is:

1. A method of detecting an isoform of human p53 protein in a biological sample of a human subject, said isoform being conformationally altered with respect to the wild-type human p53 protein, the method comprising the steps of: contacting the sample with an anti-human p53 antibody comprising a heavy chain variable region comprising CDR1 (SEQ ID NO:8), CDR2 (SEQ ID NO: 9) and CDR3 (SEQ ID NO: 10) and a light chain variable region comprising CDR1 (SEQ ID NO:11), CDR2 (SEQ ID NO: 12) and CDR3 (SEQ ID NO: 13), and detecting formation of an immunocomplex between human p53 protein and said antibody in said sample, wherein said detection indicates the presence of said isoform in said sample.

2. The method according to claim 1, wherein said heavy chain variable region comprises SEQ ID NO: 6 and said light chain variable region comprises SEQ ID NO: 7.

3. The method according to claim 1, wherein said biological sample is blood, plasma, serum, saliva, urine, neuronal cells, blood cells or other cell types.

4. The method according to claim 1, wherein said detection comprises one or more of immunoprecipitation, ELISA, RIA, immunofluorescence, Western Blot, FACS-immunocytochemistry and, immunohistochemistry.

5. The method according to claim 1, wherein the antibody comprises a heavy chain constant region and a light chain constant region.

6. The method according to claim 1, wherein said antibody is a monoclonal antibody.

7. A method of identifying dementia or a predisposition to said dementia in a subject, comprising the steps of:
(i) contacting a biological sample of the subject with an anti-human p53 antibody comprising a heavy chain variable region comprising complementary determining region (CDR) 1 (SEQ ID NO:8), CDR2 (SEQ ID NO: 9) and CDR3 (SEQ ID NO: 10) and a light chain variable region comprising CDR1 (SEQ ID NO:11), CDR2 (SEQ ID NO: 12) and CDR3 (SEQ ID NO: 13) under conditions suitable for formation of an immunocomplex between human p53 protein and said antibody; and
(ii) detecting formation of an immunocomplex of human p53 protein and said antibody, wherein said detection identifies dementia in said subject.

8. The method of claim 7, wherein said heavy chain variable region comprises SEQ ID NO: 6 and said light chain variable region comprises SEQ ID NO: 7.

9. The method of claim 7, wherein the biological sample is blood, plasma, serum, saliva, urine, neuronal cells, blood cells or other cell types.

10. The method of claim 7, wherein the detection comprises one or more of immunoprecipitation, ELISA, RIA, immunofluorescence, Western Blot, FACS, immunocytochemistry, and immunohistochemistry.

* * * * *

UNITED STATES PATENT AND TRADEMARK OFFICE
CERTIFICATE OF CORRECTION

| | | |
|---|---|---|
| PATENT NO. | : 11,208,473 B2 | Page 1 of 1 |
| APPLICATION NO. | : 17/093541 | |
| DATED | : December 28, 2021 | |
| INVENTOR(S) | : Maurizio Memo et al. | |

It is certified that error appears in the above-identified patent and that said Letters Patent is hereby corrected as shown below:

On the Title Page

Please correct the Foreign Application Priority Data under Item (30) from "TO2014000776" to --TO2014A000776--

Signed and Sealed this
Twelfth Day of August, 2025

Coke Morgan Stewart
*Acting Director of the United States Patent and Trademark Office*